(12) United States Patent
Kankan et al.

(10) Patent No.: US 8,575,393 B2
(45) Date of Patent: Nov. 5, 2013

(54) PROCESS FOR THE PREPARATION OF CINACALCET AND SALTS THEREOF, AND INTERMEDIATES FOR USE IN THE PROCESS

(75) Inventors: Rajendra Narayanrao Kankan, Maharashtra (IN); Dharmaraj Ramachandra Rao, Maharashtra (IN); Dilip Ramdas Birari, Maharashtra (IN)

(73) Assignee: CIPLA Limited, Mumbai (IN)

( * ) Notice: Subject to any disclaimer, the term of this patent is extended or adjusted under 35 U.S.C. 154(b) by 56 days.

(21) Appl. No.: 13/254,649

(22) PCT Filed: Mar. 4, 2010

(86) PCT No.: PCT/GB2010/000392
§ 371 (c)(1),
(2), (4) Date: Nov. 1, 2011

(87) PCT Pub. No.: WO2010/100429
PCT Pub. Date: Sep. 10, 2010

(65) Prior Publication Data
US 2012/0053362 A1 Mar. 1, 2012

(30) Foreign Application Priority Data
Mar. 5, 2009 (IN) .......................... 484/MUM/2009

(51) Int. Cl.
*C07C 211/00* (2006.01)
(52) U.S. Cl.
USPC ....................................................... 564/336
(58) Field of Classification Search
USPC ....................................................... 564/336
See application file for complete search history.

(56) References Cited

U.S. PATENT DOCUMENTS

| 2,996,545 | A | 8/1961 | Bottoms et al. |
| 6,011,068 | A | 1/2000 | Nemeth et al. |
| 6,211,244 | B1 | 4/2001 | Van Wagenen et al. |
| 7,294,735 | B2 | 11/2007 | Lifshitz-Liron et al. |

FOREIGN PATENT DOCUMENTS

| EP | 0915080 A1 | 5/1999 |
| EP | 0915080 A1 * | 5/1999 |
| JP | 58024545 | 2/1983 |
| WO | 2008058236 A2 | 5/2008 |
| WO | 2008063645 A1 | 5/2008 |
| WO | 2010100429 A1 | 9/2010 |

OTHER PUBLICATIONS

Kuehn, et al., Tetrahedron: Asymmetry vol. 4, No. 2, pp. 207-210, 1993.*
Foreign communication from the priority application—International Search Report and Written Opinion, PCT/GB2010/00392, Apr. 9, 2010, 15 pages.
Foreign communication from the priority application—International Preliminary Report on Patentabiilty, PCT/GB2010/00392, Apr. 9, 2010, 8 pages.
Kuehn, Michael, et al., "Analysis of chiral carboxylic acids by NMR using new optically active amines," Tetrahedron: Asymmetry, vol. 4, No. 2, pp. 207-10, XP002575167, Pergamon Press Ltd., Great Britain, (1993).
Nakahira, Hiroyuki, et al., "Preparation of bicyclic heterocyclic (fused benzamide) derivatives as renin inhibitors," Database CA (Online) Chemical Abstracts Service, Columbus, OH, 2009, XP002575168.
Wang, Xin, et al., "Synthesis of Cinacalcet congeners," Tetrahedron Letters, vol. 45, pp. 8355-8358, 2004, Science Direct, Elsevier Ltd.

* cited by examiner

*Primary Examiner* — Johann R Richter
*Assistant Examiner* — Kofi Adzamli
(74) *Attorney, Agent, or Firm* — Conley Rose, P.C.; Rodney B. Carroll

(57) ABSTRACT

There is provided a process for preparing a salt of the (R)- or (S)-isomer of 1-naphthylethylamine with mandelic acid or a derivative thereof, the process comprising reacting racemic 1-naphthylethylamine with mandelic acid or a derivative thereof to obtain the (R)- or (S)-isomer of 1-naphthylethylamine salt (III) with the acid. The salts also form an aspect of the present invention. There is also provided a salt of the (R)- or (S)-isomer of 1-naphthylethylamine with mandelic acid or a derivative thereof. There is also provided a process for preparing cinacalcet (I) or a salt thereof, the process comprising reacting an ester (II) with (R)-1-naphthylethylamine or a salt of (R)-1-naphthylethylamine and mandelic acid or a derivative thereof, to obtain cinacalcet, and optionally converting the cinacalcet to a salt thereof.

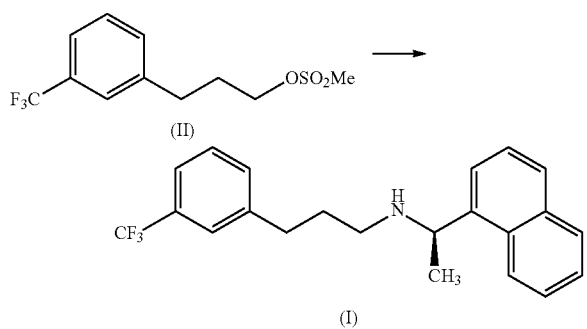

12 Claims, No Drawings

PROCESS FOR THE PREPARATION OF CINACALCET AND SALTS THEREOF, AND INTERMEDIATES FOR USE IN THE PROCESS

CROSS-REFERENCE TO RELATED APPLICATIONS

This application is a filing under 35 U.S.C. 371 of International Application No. PCT/GB2010/000392 filed Mar. 4, 2010 entitled "Process for the Preparation of Cinacalcet and Salts Thereof, and Intermediates for Use in the Process," claiming priority of Indian Patent Application No. 484/MUM/2009 filed Mar. 5, 2009, which applications are incorporated by reference herein in their entirety.

FIELD OF INVENTION

The present invention relates to a process for the preparation of cinacalcet and salts thereof, and intermediates for use in the process.

BACKGROUND OF THE INVENTION

Cinacalcet (I) belongs to a class of calcimimetic agents which decrease the secretion of parathyroid hormone ("PTH") by activating calcium receptors.

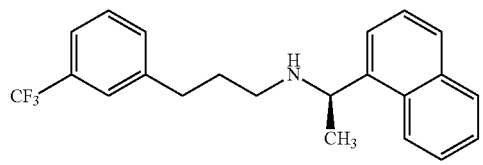

(I)

Cinacalcet may be named as (R)-N-(3-(3-(trifluoromethyl)phenyl)propyl)-1-(1-napthyl)ethylamine.

Cinacalcet hydrochloride, marketed as SENSIPAR™, is used to treat hyperparathyroidism. Calcimimetic agents increase the sensitivity of calcium receptor to calcium, which inhibits the release of parathyroid hormone and lowers parathyroid hormone levels within a short time.

U.S. Pat. No. 6,011,068 discloses inorganic ion receptors, specifically calcium receptors.

U.S. Pat. No. 6,211,244 specifically discloses cinacalcet, its pharmaceutically acceptable salt or complex and a process for the preparation of it. However, the process disclosed in U.S. Pat. No. 6,211,244 involves the use of flammable and toxic reagents such as titanium isopropoxide, ethanolic or methanolic cyanoborohydride.

It is observed that cinacalcet obtained by the prior art process is not absolutely pure. It may contain traces of starting material, solvent contaminations, side products and byproducts generated during the reaction. Such impurities result in a decrease in the purity of the final product, hence they are undesirable.

X. Wang et. al, Tetrahedron Letters 45 (2004) 8355-8358, teach that they have identified two new isomeric dihydronaphthalene impurities.

The inventors of US20070060645 have identified an impurity generated during the synthesis of cinacalcet and designated it as cinacalcet carbamate impurity. US20070060645 further describes a HPLC method to detect the carbamate impurity. However, it does not provide any method of minimizing the carbamate impurity.

WO2008058236 describes a desfluoro impurity generated during the synthesis of cinacalcet that can be detected at a relative retention time (RRT) of 0.9 during HPLC analysis.

All the impurities described in the above prior art references are undesirable and need to be removed so as to obtain a higher purity final product. Hence, there is a need to develop a process for the preparation of cinacalcet that is simple, avoids generation of impurities, is easy to scale up and involves the use of reagents that are readily available and safe to handle.

(R)-1-naphthylethylamine is a key intermediate in the synthesis of cinacalcet and its salts. It can be obtained by resolution of racemic 1-naphthylethylamine. U.S. Pat. No. 2,996,545 describes a method of resolution of 1-naphthylethylamine using d-tartaric acid in the presence of methanol to obtain the corresponding tartrate salt. The tartrate salt is purified by fractional crystallization to obtain crystalline optically pure (R)-1-naphthylethylamine. The crystallization steps need to be repeated a number of times until a constant optical rotation and the desired optical purity is obtained. Repeated crystallizations are difficult to carry out industrially and result in material loss. Also, the (R)-1-naphthylethylamine is obtained as an oily residue which needs to be further isolated by distillation. This affects the final yield of the product.

U.S. Pat. No. 2,996,545 further describes that L-malic acid and D-camphoric acid have been used for resolution of racemic amines. Both these optically active acids are expensive. It further states that L-malic acid is found unsatisfactory particularly for resolution of naphthylethylamine as it is expensive, its recovery for re-use is difficult and losses of material are high. Further, the purification of amine malate salt is tedious, expensive and never complete which results in partially resolved amines.

JP58024545 discloses the use of cis-2-benzamidocyclohexane carboxylic acid as a resolving agent for resolution of 1-naphthylethylamine.

There has been no disclosure of a simple and industrially-suitable method for resolution of 1-naphthylethylamine. The present invention provides a process for the resolution of 1-naphthylethylamine and also describes a new method of synthesis of cinacalcet and salts thereof.

SUMMARY OF THE INVENTION

According to a first aspect of the present invention, there is provided a process for preparing a salt of the (R)- or (S)-isomer of 1-naphthylethylamine with a chiral acid, the process comprising reacting racemic 1-naphthylethylamine with a chiral acid to obtain the (R)- or (S)-isomer of 1-naphthylethylamine salt with the acid, wherein the chiral acid is mandelic acid or a derivative thereof. Thus, the present invention provides a process for preparing either (R)-1-naphthylethylamine mandelate, or (S)-1-naphthylethylamine mandelate. In an alternative aspect, the process may be used to prepare a salt of the (R)- or (S)-isomer of 1-naphthylethylamine with a derivative of mandelic acid.

In an embodiment, the chiral acid is mandelic acid, preferably D-(−)-mandelic acid.

In an embodiment, the solvent is ethanol, isopropyl alcohol or acetone.

In an embodiment, the solvent is ethanol and the product of the reaction is a salt of the (R)-isomer. In an alternative embodiment, the solvent is isopropyl alcohol or acetone and the product of the reaction is a salt of the (S)-isomer.

In an embodiment, the acid is (D)-(−)-mandelic acid and the molar ratio of D-(−)-mandelic acid to (R)- or (S)-1-naphthylethylamine ranges from 0.4 to 1.2, preferably 0.7 to 1.0 molar equivalents, most preferably the ratio is 1.0 molar equivalent.

In another embodiment, the salt of (R)- or (S)-1-naphthylethylamine may be purified using the same solvent as used for the preparation of the salt, for example ethanol, isopropyl alcohol or acetone. In an embodiment, the (R)- or (S)-1-naphthylethylamine salt is suspended in the solvent and heated to a temperature ranging from 50 to 60° C. until a clear solution is obtained. The clear solution may then be then cooled to a temperature ranging from 25 to 30° C. to isolate (R)-1-naphthylethylamine salt.

In an embodiment, the (R)- or (S)-1-naphthylethylamine salt obtained is in substantially pure isomeric form. Within the scope of the present invention, "substantially pure isomeric form" means essentially free of other isomeric forms of 1-naphthylethylamine. "Substantially pure isomeric form" may mean having undesired isomeric impurities of less than 5%, preferably less than 3%, more preferably less than 1%, most preferably less than 0.5%.

In an embodiment, the (R)- or (S)-1-naphthylethylamine mandalate salt has a chiral purity of at least 99.0%, preferably at least 99.3%, more preferably at least 99.5%. In the context of this specification, chiral purity is calculated as follows:

100×[(R-isomer)/(R-isomer+S-isomer)]

where "(R-isomer)" in the above formula refers to the molar quantity of the R-isomer and "(S-isomer)" in the above formula refers to the molar quantity of the S-isomer. Chiral purity may be measured using a chiral column. The identification of the enantiomers is based on the retention time of an authentic standard used as a reference. The calculations are by a peak area normalisation method.

According to another aspect of the present invention, there is provided a salt of the (R)- or (S)-isomer of 1-naphthylethylamine with a chiral acid, wherein the chiral acid is mandelic acid or a derivative thereof.

In an embodiment, the salt is a salt of (R)-1-naphthylethylamine with the chiral acid. In an alternative embodiment, the salt is a salt of (S)-1-naphthylethylamine with the chiral acid.

In an embodiment, the chiral acid is mandelic acid, preferably D-mandelic acid. Preferably, there is provided a salt of D-mandelic acid and (R)-1-naphthylethylamine.

According to another aspect of the present invention, there is provided a process for interconverting the (R)- and (S)-isomers of 1-naphthylethylamine. In an embodiment, the (R)- or (S)-isomer is racemised to racemic 1-naphthylethylamine and then converted to the desired isomer according to a process described above. In an embodiment, a suitable interconversion process comprises: (i) preparing a salt of (R)-naphthylethylamine with mandelic acid as described above, whereby a mother liquor enriched in (S)-naphthylethylamine is obtained; (ii) converting (S)-naphthylethylamine obtained from step (i) to racemic naphthylethylamine; and (iii) if desired, using racemic (S)-naphthylethylamine obtained from step (ii) in a process as described above.

Cinacalcet is a compound in the form of the R-enantiomer. In an embodiment, the salt of 1-naphthylethylamine is in the form of the (R)-enantiomer. The (R)-enantiomer may be used in a process for preparing cinacalcet. The process may be as described below. Alternatively, the salt of 1-naphthylethylamine is in the form of the (S)-enantiomer. The (S)-enantiomer may be used in a process for preparing a compound which is the opposite enantiomer of cinacalcet, the process for preparing the opposite enantiomer of cinacalcet being carried out in accordance with the process steps and conditions described below.

According to another aspect of the present invention, there is provided a process for preparing cinacalcet (I) or a salt thereof, the process comprising reacting an ester (II) with either (R)-1-naphthylethylamine or a salt of a chiral acid with (R)-1-naphthylethylamine, to obtain cinacalcet, and optionally converting the cinacalcet to a salt thereof.

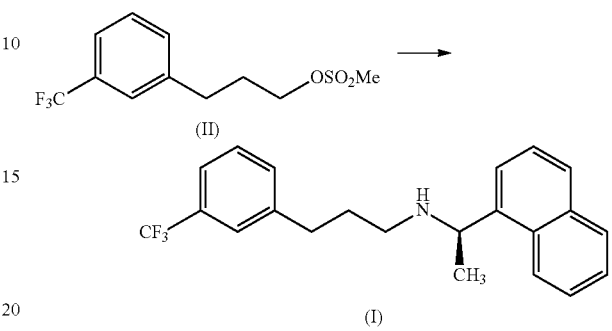

Preferably, the solvent for the reaction of ester (II) with the (R)-1-naphthylethylamine or salt thereof is water.

In an embodiment, the process comprises reacting (R)-1-naphthylethylamine with ester (II) in the presence of water as the solvent. Suitably, no organic solvents are present in the reaction mass.

In an embodiment, the chiral acid is mandelic acid, a derivative of mandelic acid, tartaric acid, a derivative of tartaric acid, malic acid or D-camphoric acid. The acid is chiral, so the acid will be in the form of an isomer. Therefore, the chiral acid may be D- or L-mandelic acid, the D- or L-isomer of a derivative of mandelic acid, D- or L-tartaric acid, the D- or L-isomer of a derivative of tartaric acid, D- or L-malic acid or D- or L-camphoric acid. Suitably, the chiral acid may be D-mandelic acid, L-malic acid or D-camphoric acid.

Preferably, the chiral acid is mandelic acid or a derivative of mandelic acid. More preferably, the chiral acid is an isomer of mandelic acid. The salt of (R)-1-naphthylethylamine with (D)-mandelic acid has surprisingly advantageous properties, so, preferably, the chiral acid for use in the above process is D-(−)-mandelic acid.

In an embodiment, the cinacalcet or salt thereof has an HPLC purity greater than 95%, preferably greater than 97%, more preferably greater than 99%, still more preferably greater than 99.5%. Preferably, the impurities generated during the prior art syntheses of cinacalcet hydrochloride are not detected in the product of the present invention.

In an embodiment, the cinacalcet is converted to a salt thereof. Suitably, the cinacalcet is converted to cinacalcet hydrochloride. Cinacalcet may be converted to cinacalcet hydrochloride by reacting the cinacalcet with HCl. The HCl may be in the form of a solution with isopropyl alcohol or as dry HCl gas.

In an embodiment, the cinacalcet or salt thereof is isolated and subsequently purified, for example by recrystallisation. Typically, the cinacalcet is converted to cinacalcet hydrochloride which is then recrystallized by dissolving in a suitable organic solvent at the reflux temperature of the solvent, cooling the solution, for example to a temperature ranging from 20 to 30° C., typically under stirring, optionally further cooling the solution for example to a temperature of less than 10° C. and isolating the precipitated solid.

Advantageously, the purity of the purified cinacalcet or salt thereof according to HPLC is greater than 99.0%, preferably greater than 99.5%, more preferably greater than 99.9%.

Suitably, the reaction is carried out in the presence of a base. The base may be an organic base or an inorganic base. The organic base may be an aliphatic or aromatic amine. Preferably, the aliphatic amine is triethylamine, tributylamine, diisopropylethylamine or pyridine. Preferably, the inorganic base is an alkali metal hydroxide, alkali metal alkoxide, alkali metal carbonate or alkali metal bicarbonate. Preferably, the alkali carbonate is sodium or potassium carbonate. Most preferably, the base used is potassium carbonate.

In an embodiment, the reaction of ester (II) with the salt of (R)-1-naphthylethylamine is carried out in the absence of an organic solvent.

In an embodiment, the ester (II) is prepared by esterifying 3-(3-trifluoromethylphenyl)propan-1-ol to obtain the ester. The 3-(3-trifluoromethylphenyl)propan-1-ol may be obtained by reducing 3-(3-trifluoromethylphenyl)propanoic acid to obtain 3-(3-trifluoromethylphenyl)propan-1-ol. The 3-(3-trifluoromethylphenyl)propanoic acid may be obtained by reducing 3-trifluoromethyl cinnamic acid.

Thus, in a preferred embodiment, the ester (II) is prepared by reducing 3-trifluoromethyl cinnamic acid to obtain 3-(3-trifluoromethylphenyl)propanoic acid, reducing the 3-(3-trifluoromethylphenyl)propanoic acid to 3-(3-trifluoromethylphenyl)propan-1-ol and esterifying the 3-(3-trifluoromethylphenyl)propan-1-ol.

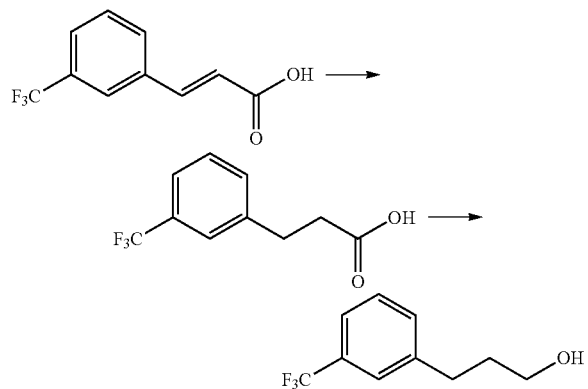

The reduction of 3-trifluoromethyl cinnamic acid may be carried out by a catalytic hydrogenation for example using platinum dioxide, Raney Nickel or Pd/C as the catalyst, or in the presence of a reducing agent for example sodium borohydride or lithium aluminium hydride. Preferably, the reduction is carried out by catalytic hydrogenation. The preferred catalyst is Pd/C.

The reduction of 3-(3-trifluoromethylphenyl)propanoic acid may be carried out in the presence of a suitable reducing agent. The reducing agent may be selected from borane gas, diborane, borane dimethyl sulfide. The preferred reducing agent is borane dimethyl sulfide. The reaction mixture may be acidified, typically with HCl and 3-(3-trifluoromethylphenyl)propan-1-ol may be isolated by extracting the reaction mass with a suitable organic solvent.

According to another aspect of the present invention, there is provided a process for preparing ester (II), the process comprising reducing 3-(3-trifluoromethylphenyl)propanoic acid to obtain 3-(3-trifluoromethylphenyl)propan-1-ol in the presence of borane dimethyl sulfide, and esterifying 3-(3-trifluoromethylphenyl)propan-1-ol to obtain the ester.

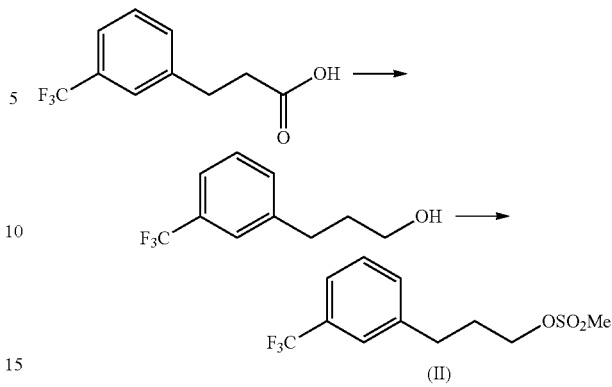

According to another aspect of the present invention, there is provided cinacalcet or a salt thereof prepared according to any one of the processes described above.

According to another aspect of the present invention, there is provided cinacalcet or a salt thereof prepared according to any one of the processes described above.

According to another aspect of the present invention, there is provided a pharmaceutical composition comprising cinacalcet or a salt thereof prepared according to any one of the processes described above, together with one or more pharmaceutically acceptable excipients.

According to another aspect of the present invention, there is provided cinacalcet or a salt thereof prepared according to any one of the processes described above, or a pharmaceutical composition as described above, for use in medicine.

According to another aspect of the present invention, there is provided cinacalcet or a salt thereof prepared according to any one of the processes described above, or a pharmaceutical composition as described above, for use in treating hyperparathyroidism.

According to another aspect of the present invention, there is provided the use of cinacalcet or a salt thereof prepared according to any one of the processes described above, or a pharmaceutical composition as described above, for use in the manufacture of a medicament for treating hyperparathyroidism.

According to another aspect of the present invention, there is provided a method of treating hyperparathyroidism comprising administering to a subject in need thereof a therapeutically acceptable amount of cinacalcet or a salt thereof prepared according to any one of the processes described above.

DETAILED DESCRIPTION OF THE INVENTION

It is clear from the prior art references that there may be various impurities produced during the synthesis of cinacalcet. These impurities are difficult to separate by conventional methods because of their close structural similarity to cinacalcet. The structures of these impurities can be represented as follows:

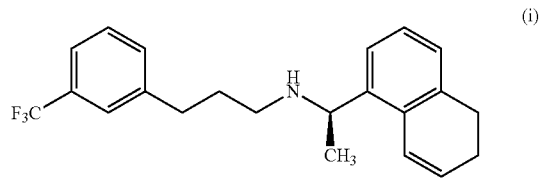

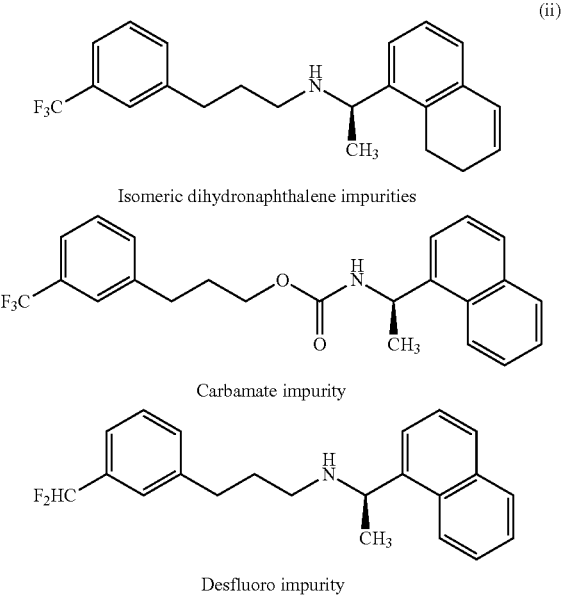

Isomeric dihydronaphthalene impurities

Carbamate impurity

Desfluoro impurity

The present invention provides a simple and industrially-scaleable process for the preparation of cinacalcet that does not generate the above impurities.

In a preferred embodiment, the present invention provides a process for the preparation of cinacalcet or a salt thereof. The process comprises reaction of cinacalcet active ester (II) with (R)-1-naphthylethylamine or a chiral salt thereof to obtain cinacalcet or a salt thereof.

The reaction of compound of formula (II) and (III) is shown in Scheme 1 below.

Scheme 1

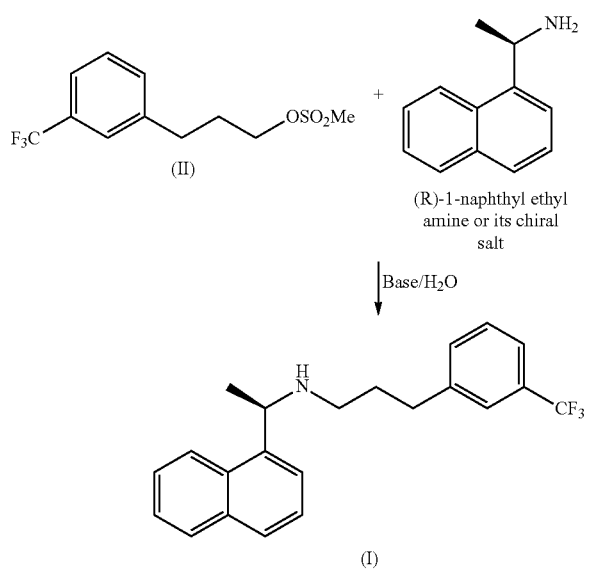

In another preferred embodiment of the present invention, the solvent used for the reaction of compound of formula (II) with (R)-1-naphthylethylamine or the chiral salt thereof is water. The process of the present invention avoids the use of any organic solvents for the reaction which makes the process environmentally friendly. The use of water as a solvent aids to eliminate the formation of impurities that are generated by the prior art processes.

The above reaction can be carried out in the presence of a base. The base can be an organic base or an inorganic base. A preferred organic base is selected from the group consisting of aliphatic and aromatic amines. Preferably, the aliphatic amine is triethylamine, tributylamine, diisopropylethylamine or pyridine. A preferable inorganic base is either an alkali metal hydroxide or alkali metal alkoxide or alkali metal carbonate or alkali metal bicarbonate. Preferably, the alkali carbonate is either sodium or potassium carbonate. Most preferably, the base used is potassium carbonate.

In an embodiment, water and the base are added to the compound of formula (II) at a temperature of 20-30° C. under stirring. The mixture is heated at a temperature of 60-70° C. to get a suspension. To this suspension, (R)-1-naphthylethylamine or its chiral salt is added under stirring while maintaining the temperature of 60-70° C. until the reaction is complete. After completion of the reaction, the reaction mass is cooled to 20-30° C. and extracted with a suitable organic solvent such as ethyl acetate, toluene, dichloromethane, heptane or hexane or a mixture thereof. The organic layer is separated and the solvent is removed from the organic layer completely by distillation under vacuum to obtain cinacalcet base (I).

Cinacalcet (I) may be converted to cincalcet hydrochloride for example by stirring cinacalcet with IPA/HCl or dry HCl gas at a temperature of 20-30° C. The solvent is removed completely from the reaction mass by distillating at a temperature of 50-60° C. to get a residue. The residue is further suspended in a suitable solvent or a solvent mixture and heated to the reflux temperature of the solvent or the solvent mixture to get a clear solution. The clear solution is stirred and cooled to a temperature of less than 10° C. Preferably, the cooling temperature is in the range of 0-10° C., most preferably in the range of 0-5° C. whereby cinacalcet hydrochloride precipitates. Suitably, the precipitated solid is filtered and dried at a temperature of 50-65° C. to obtain cinacalcet hydrochloride.

The solvent may be ethyl acetate or a solvent mixture such as a mixture of ethanol and diisopropyl ether, a mixture of methanol and heptane, a mixture of isopropyl alcohol and heptane or a mixture of toluene and hexane. Most preferably, the solvent is ethyl acetate.

Cinacalcet hydrochloride may be recrystallized further by dissolving in a suitable organic solvent at the reflux temperature of the solvent, cooling to a temperature of 20-30° C. under stirring. The reaction mass may be further cooled to a temperature of less than 10° C., preferably in the range of 0-10° C., most preferably in the range of 0-5° C. to obtain a solid. The solid is dried under vacuum to obtain pure cinacalcet hydrochloride (HPLC purity >99.9%).

In another aspect, the present invention provides a method of resolution of 1-naphthylethylamine in the form of the (R)-isomer of 1-naphthylethylamine salt. The process comprises reacting racemic 1-naphthylethylamine with a chiral acid to obtain the corresponding (R)-1-naphthylethylamine salt (III) with the acid. The product is used as a key intermediate in the synthesis of cinacalcet as described hereinbefore.

The preparation of (R)-1-naphthylethylamine salt can be shown as in Scheme 2 as follows:

Scheme 2

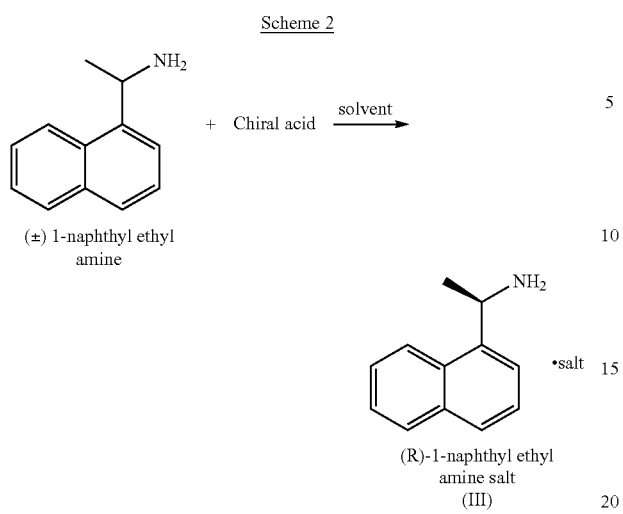

In an embodiment, the chiral acid used for resolution of (R)-1-naphthylethylamine (III) is selected from an isomer of mandelic acid, or derivatives thereof, or an isomer of tartaric acid or derivatives thereof. Most preferably, the chiral acid used is D-(−)-mandelic acid. The resolution process and the product thereof is highly advantageous as it is simple and affords the product in high purity. Mandelic acid is the most preferred acid.

The molar ratio of D-(−)-mandelic acid to 1-naphthylethylamine may range from 0.4 to 1.2, preferably 0.7 to 1.0 molar equivalents, most preferably the ratio is 1.0 molar equivalent.

In yet another embodiment, the chiral salt of (R)-1-naphthylethylamine may be purified using the same solvent as described herein above. The (R)-1-naphthylethylamine salt is suspended in the solvent and heated at a temperature of 50-60° C. until a clear solution is obtained. The clear solution is then cooled gradually to 25-30° C. to isolate the (R)-1-naphthylethylamine salt.

In an embodiment, the (R)-1-naphthylethylamine mandalate salt has a chiral purity of at least 99.5%.

In an embodiment, the (S)-isomer of 1-naphthylethylamine salt can be obtained by reacting racemic 1-naphthylethylamine with a chiral acid in the presence of isopropyl alcohol or acetone to obtain the corresponding (S)-1-naphthylethylamine chiral salt (III). This (S)-isomer may be used as an intermediate in the synthesis of (S)-cinacalcet.

The (R)- and (S)-isomers of 1-naphthylethylamine salt may be interconverted by forming a racemic 1-naphthylethylamine salt first and then converting it to the desired isomer by using a suitable solvent.

Table 1 below describes the effect of solvents on the resolution of 1-naphthylethylamine mandalate salt.

TABLE 1

| Solvent | Product | Chiral purity (%) |
| --- | --- | --- |
| Ethanol | R-(+)-isomer | >99.6% |
| Isopropyl alcohol | S-(−)-isomer | >99.2% |
| Acetone | S-(−)-isomer | >98.1% |
| Ethyl acetate | Racemic mixture | |

Another important intermediate used in the process of the present invention is the compound of formula (II). It may be prepared as described in the Scheme 3 as follows:

Scheme 3

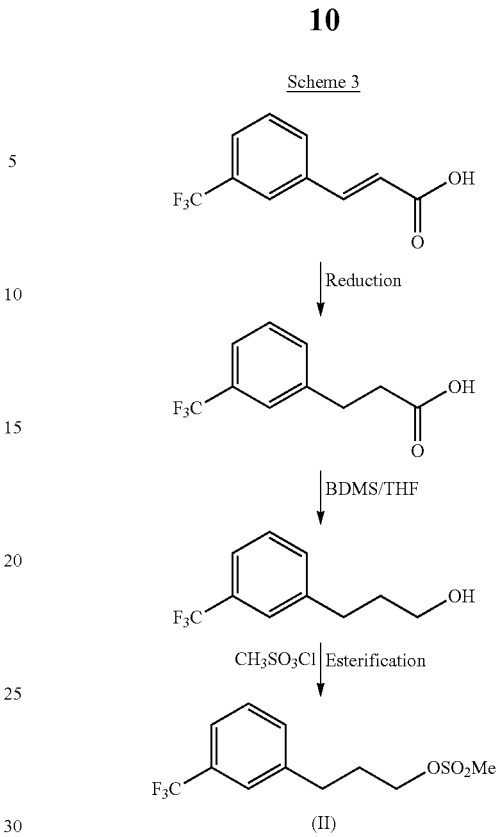

The starting compound i.e. 3-trifluoromethyl cinnamic acid is reduced to obtain 3-(3-trifluoromethylphenyl)propanoic acid. The reduction may be carried out by a catalytic hydrogenation for example using platinum dioxide, Raney Nickel or Pd/C as the catalyst or in the presence of a reducing agent for example sodium borohydride or lithium aluminium hydride. Preferably, the reduction is carried out by catalytic hydrogenation. The preferred catalyst is Pd/C.

Typically, the reduction is carried out at a temperature of 20-30° C. The $H_2$ pressure is typically 1 kg/cm$^2$. Typically, the reduction is carried out for a period of time ranging from 5 to 15 hours.

The solvent used in the reduction reaction may be a $C_{1-6}$ alcohol such as methanol, ethanol or isopropyl alcohol. The preferred solvent is methanol.

3-(3-trifluoromethylphenyl)propanoic acid may be further reduced to 3-(3-trifluoromethylphenyl)propan-1-ol using a suitable reducing agent. The reducing agent may be selected from borane gas, diborane, borane dimethyl sulfide. The preferred reducing agent is borane dimethyl sulfide.

The solvent used for the reduction may be selected from tetrahydrofuran or an ether solvent such as diethyl ether, diisopropyl ether or methyl tert-butyl ether. The preferred solvent is tetrahydrofuran.

The reduction may be carried out at a temperature of less than 10° C. Preferably, the cooling temperature ranges from 0 to 10° C., most preferably from 0 to 5° C.

The reaction mixture may be acidified, typically with HCl, and the 3-(3-trifluoromethylphenyl)propan-1-ol may be isolated by extracting the reaction mass with a suitable organic solvent. The solvent may be removed for example by distillation to obtain 3-(3-trifluoromethylphenyl)propan-1-ol as a residue.

The solvent may be a hydrocarbon solvent such as hexane, heptane, toluene, ethyl acetate or dichloromethane, preferably toluene.

3-(3-trifluoromethylphenyl)propan-1-ol may be further suspended in a suitable solvent and cooled to a temperature ranging from 20 to 30° C. A suitable base and an esterifying agent may be added to the reaction mass under stirring, while maintaining the temperature of the reaction.

After completion of the reaction, the reaction mixture may be filtered and the organic layer separated. The organic layer may be acidified, typically with HCl. The product of formula (II) can be isolated as a residue for example by distilling out the solvent from the reaction mass.

The solvent for esterification may be a hydrocarbon solvent such as ethyl acetate, dichloromethane, toluene, hexane or heptane, preferably toluene.

The base used for esterification may be an organic base or an inorganic base. A preferred organic base is selected from the group consisting of aliphatic and aromatic amines. Preferably, the aliphatic amine is triethylamine, tributylamine, diisopropylethylamine and pyridine. Most preferable base is triethylamine.

An esterifying agent may be selected from an acid halide such as methane sulfonyl chloride, p-toluyl sulfonyl chloride.

The isolated active ester compound of formula (II) may be used as an intermediate in the synthesis of cinacalcet.

EXAMPLES

There follow, by way of non-restrictive explanation of the present invention, the following examples.

Example 1

Preparation of 3-(3-trifluoromethylphenyl)propanoic acid 3-trifluoromethyl cinnamic acid (0.463 moles, 100 gms) was dissolved in 1.0 lt. of methanol and charged to a hydrogenating vessel. 5% Pd/C (3 gms) was added. The reaction mass was hydrogenated at H2 pressure of 1 kg/cm2 at a temperature of 25° C. for about 10 hours. After completion of the reaction, the contents of the vessel was filtered, washed with methanol (100 ml). Methanol was evaporated from the filtered material to get a residue of 3-(3-trifluoromethylphenyl)propanoic acid (100 gms, Yield 100%).

Example 2

Preparation of 3-(3-trifluoromethylphenyl)propan-1-ol

Compound obtained from Example 1 (0.463 moles, 100 gms) was suspended in 500 ml of tetrahydrofuran under stirring. The reaction mass was cooled to 0-5° C. 94% solution of borane dimethyl sulfide solution (0.62 moles, 50 ml) was added drop wise maintaining the temperature of 0-5° C. The reaction mass was stirred at 25-30° C. for about 10 hours. 10% HCl (100 ml) was added drop wise to the reaction mass at 25-30° C. in about 2 hours and then extracted with toluene (2×250 ml). The organic layer was separated and washed with water (5×500 ml). Toluene was removed completely from the organic layer by distillation under vacuum to isolate the title compound as an oil (85 gms, Yield 90%).

Example 3

Preparation of 3-(3-trifluoromethylphenyl)propan-1-methane sulfonate-ester (II)

The title compound of Example 2 (0.416 moles, 85 gms) was suspended in toluene at 25-30° C., cooled to 20° C. Triethylamine (0.75 moles, 105 ml) was added at 20-25° C. under stirring. A solution of methane sulfonyl chloride in toluene (0.55 moles, 63 gms in 90 ml) was added drop wise to the reaction mass within 2 hours. The reaction mass was filtered and washed with toluene (2×100 ml). The organic layer was separated, washed with 1N HCl (2×100 ml) and then with water. Toluene was distilled out under vacuum from the organic layer to get the title compound as an oil (110 gms, Yield 93%).

Example 4

Preparation of (R)-1-naphthylethylamine mandalate salt

Racemic 1-naphthylethylamine (2.63 moles, 450 gms) was suspended in ethanol (3.1 lts). D-mandelic acid (2.63 moles, 400 gms) was added under stirring. Pure (R)-naphthylethylamine mandalate (3-4 gms) was added as a seed and heated at 55-60° C. until a clear solution was obtained. The solution was cooled gradually to 25-30° C. and stirred for about 12 hours to obtain a solid. The solid was suspended in ethanol (2.3 lts) and heated at a temperature of 55-60° C. for about half an hour. The suspension was cooled gradually to 25-30° C. and stirred to obtain a solid. The solid was washed with ethanol and dried at 50-55° C. to obtain the title compound (250 gms, Yield 70%, chiral purity >99.0%).

Example 5

Preparation of (S)-1-naphthylethylamine mandalate salt

Racemic 1-naphthylethylamine (2.63 moles, 450 gms) was suspended in isopropyl alcohol (3.1 lts). D-mandelic acid (1.32 moles, 200 gms) was added under stirring and heated at 55-60° C. until a clear solution was obtained. The solution was cooled gradually to 25-30° C. and stirred for about 12 hours to obtain a solid. The solid was suspended in isopropyl alcohol (2.3 lts) and heated at a temperature of 55-60° C. for about half an hour. The suspension was cooled gradually to 25-30° C. and stirred to obtain a solid. The solid was washed with isopropyl alcohol and dried at 50-55° C. to obtain the title compound (225 gms, Yield 62%, chiral purity >99.0%).

Example 6

Preparation of cinacalcet base—from a salt of (R)-1-naphthylethylamine

Purified water (400 ml) was taken in a reaction vessel. Potassium carbonate (0.77 moles, 107 gms) and the product of Example 3 (0.39 moles, 110 gms) were added under stirring. The reaction mixture was heated to 60-65° C. The compound obtained from example 4 (0.26 moles, 83 gms) was added maintaining the temperature of the reaction mass at 60-65° C. for 20 hours under stirring. After cooling the mass to a temperature of 20-25° C., ethyl acetate (850 ml) was added and stirred. The separated organic layer was washed with purified water (2×400 ml) and then washed with saturated brine solution (2×400 ml). The solvent was removed from the organic layer by distillation under vacuum to obtain cinacalcet base (91 gms, yield 100%).

Example 7

Preparation of cinacalcet base—from (R)-1-naphthylethylamine free base

Purified water (375 ml) was taken in a reaction vessel. Potassium carbonate (0.88 moles, 121 gms) and the product of Example 3 (0.53 moles, 150 gms) was added under stirring. The reaction mixture was heated to 60-65° C. (R)-1-naphthylethylamine (0.44 moles, 75 gms) was added maintaining the temperature of the reaction mass at 60-65° C. for about 17 hours under stirring. After cooling the mass to a temperature of 20-25° C., ethyl acetate (2×250 ml) was added and stirred. The separated organic layer was washed with purified water (2×300 ml) and then with saturated brine solution (2×300 ml). The solvent was removed from the organic layer by distillation under vacuum to obtain cinacalcet base (97 gms).

Example 8

Preparation of Cinacalcet Hydrochloride

Cinacalcet (0.25 moles, 91 gms) was taken in a reaction vessel and IPA/HCl (85 ml) was added dropwise and stirred for about 15 minutes. The solvent was distilled at 50-55° C. under high vacuum to obtain a residue. The residue was suspended in ethyl acetate (516 ml) and heated to reflux temperature until a clear solution was obtained and the solution stirred for about 30 minutes. The solution was cooled to 0-5° C. and stirred to obtain a solid. The solid was washed with ethyl acetate (2×85 ml) and dried at 55-60° C. to obtain the title compound (70 gms, Yield 70%, HPLC purity=98.5%).

Example 9

Preparation of Cinacalcet Hydrochloride

Purified water (200 ml) was taken in a reaction vessel. Potassium carbonate (0.39 moles, 54 gms) and the product of Example 3 (0.19 moles, 55 gms) were added under stirring. The reaction mixture was heated to 60-65° C. The compound obtained from example 4 (0.13 moles, 42 gms) was added maintaining the temperature of the reaction mass at 60-65° C. for 20 hours under stirring. After cooling the mass to a temperature of 20-25° C., ethyl acetate (420 ml) was added and stirred. The separated organic layer was washed with purified water (2×200 ml) and then with saturated brine solution (2×200 ml). To the organic layer IPA/HCl (45 ml) added dropwise and stirred for about 30 minutes. The solvent was distilled at 50-55° C. under high vacuum to obtain a residue. The residue was suspended in ethyl acetate (260 ml) and heated to reflux temperature until a clear solution was obtained and the solution stirred for about 30 minutes. The solution was cooled to 0-5° C. and stirred to obtain a solid. The solid was washed with chilled ethyl acetate (2×45 ml) and dried at 55-60° C. to obtain the title compound (36 gms).

Example 10

Purification of Cinacalcet Hydrochloride

Cinacalcet hydrochloride (70 gms) was dissolved in ethyl acetate (700 ml) at reflux temperature. The solvent was distilled out partially at 80° C. The suspension was cooled and stirred for about 2-3 hours. The suspension was further chilled to 0-5° C. and stirred for about 2 hours to obtain a solid. The solid was washed with chilled ethyl acetate and dried at 55-60° C. to obtain cinacalcet hydrochloride (64 gms, HPLC purity=99.96%, Chiral purity=99.0%).

It will be appreciated that the invention may be modified within the scope of the appended claims.

The invention claimed is:

1. A process for preparing cinacalcet (I) or a salt thereof, the process comprising reacting an ester (II) with a salt of mandelic acid with (R)-1-naphthylethylamine, to obtain cinacalcet, and optionally converting the cinacalcet to a salt thereof

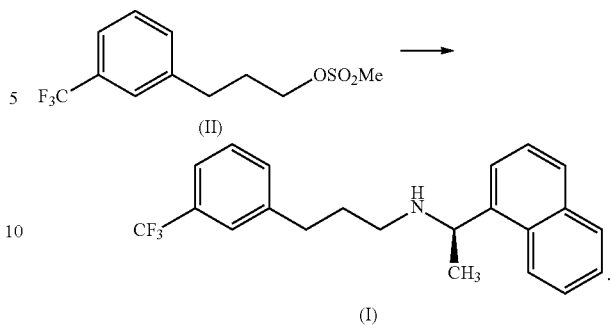

2. The process according to claim 1, wherein the solvent for the reaction of ester (II) with the salt is water.

3. The process according to claim 1, wherein the chiral acid is D-(−)-mandelic.

4. The process according claim 1, wherein the cinacalcet is converted to a salt thereof.

5. The process according to claim 4, wherein the cinacalcet is converted to cinacalcet hydrochloride.

6. The process according to claim 1, wherein the cinacalcet or salt thereof is isolated and subsequently recrystallised.

7. The process according to claim 1, wherein the reaction is carried out in the presence of a base selected from an organic base and an inorganic base.

8. The process according to claim 7, wherein the base is selected from the group consisting of triethylamine, tributylamine, diisopropylethylamine, pyridine, sodium carbonate and potassium carbonate.

9. The process according to claim 1, wherein the ester (II) is prepared by reducing 3-trifluoromethyl cinnamic acid to obtain 3-(3-trifluoromethylphenyl) propanoic acid, reducing the 3-(3-trifluoromethylphenyl) propanoic acid to 3-(3trifluoromethylphenyl) propan-1-ol and esterifying the 3-(3-trifluoromethylphenyl) propan-1-ol

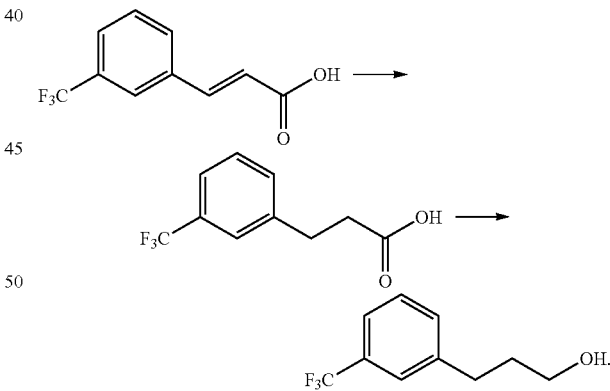

10. The process according to claim 1, wherein the reaction of ester (II) with the salt of (R)-1-naphthylethylamine is carried out in the absence of an organic solvent.

11. The process according to claim 1, wherein the salt of mandelic acid with (R)-1-naphthylethylamine is prepared according to a process comprising reacting racemic 1-naphthylethylamine with mandelic acid to obtain the (R)-isomer of 1-naphthylethylamine salt with the acid.

12. A process utilizing a salt of the (R)- or (S)-isomer of 1-naphthylethylamine with mandelic acid for preparing cinacalcet or a salt thereof.

* * * * *

UNITED STATES PATENT AND TRADEMARK OFFICE
CERTIFICATE OF CORRECTION

PATENT NO.        : 8,575,393 B2
APPLICATION NO. : 13/254649
DATED             : November 5, 2013
INVENTOR(S)       : Kankan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 112 days.

Signed and Sealed this
Twenty-second Day of September, 2015

Michelle K. Lee
*Director of the United States Patent and Trademark Office*